United States Patent [19]
Swanson

[11] Patent Number: 5,782,826
[45] Date of Patent: Jul. 21, 1998

[54] SYSTEM AND METHODS FOR DETECTING ANCILLARY TISSUE NEAR TISSUE TARGETED FOR ABLATION

[75] Inventor: David K. Swanson, Mountain View, Calif.

[73] Assignee: EP Technologies, Inc., San Jose, Calif.

[21] Appl. No.: 742,628

[22] Filed: Nov. 1, 1996

[51] Int. Cl.$^6$ .................................................. A61B 17/39
[52] U.S. Cl. ............................................................ 606/34
[58] Field of Search .......................... 607/122; 606/34, 606/41, 42

[56] References Cited

U.S. PATENT DOCUMENTS

| | | | |
|---|---|---|---|
| 5,391,199 | 2/1995 | Ben Haim | 607/122 |
| 5,450,846 | 9/1995 | Goldreyer | 607/122 |
| 5,500,012 | 3/1996 | Brucker et al. | 607/122 |
| 5,546,940 | 8/1996 | Panescu et al. | 606/41 |
| 5,598,848 | 2/1997 | Swanson et al. | 607/122 |

*Primary Examiner*—William E. Kamm
*Assistant Examiner*—George R. Evanisko
*Attorney, Agent, or Firm*—Oppenheimer Poms Smith

[57] ABSTRACT

Systems and methods detect ancillary tissue within a tissue region targeted for ablation by locating a region to apply ablation energy to tissue targeted for ablation and applying energy within the region to stimulate selected ancillary tissue not targeted for ablation. The systems and methods sense when the selected ancillary tissue is affected by the stimulant energy within the region, thereby determining the presence of such ancillary tissue within the region. The systems and methods relocate the region until the selected ancillary tissue is not affected by the stimulant energy. The systems and methods then apply ablation energy in the region.

29 Claims, 1 Drawing Sheet

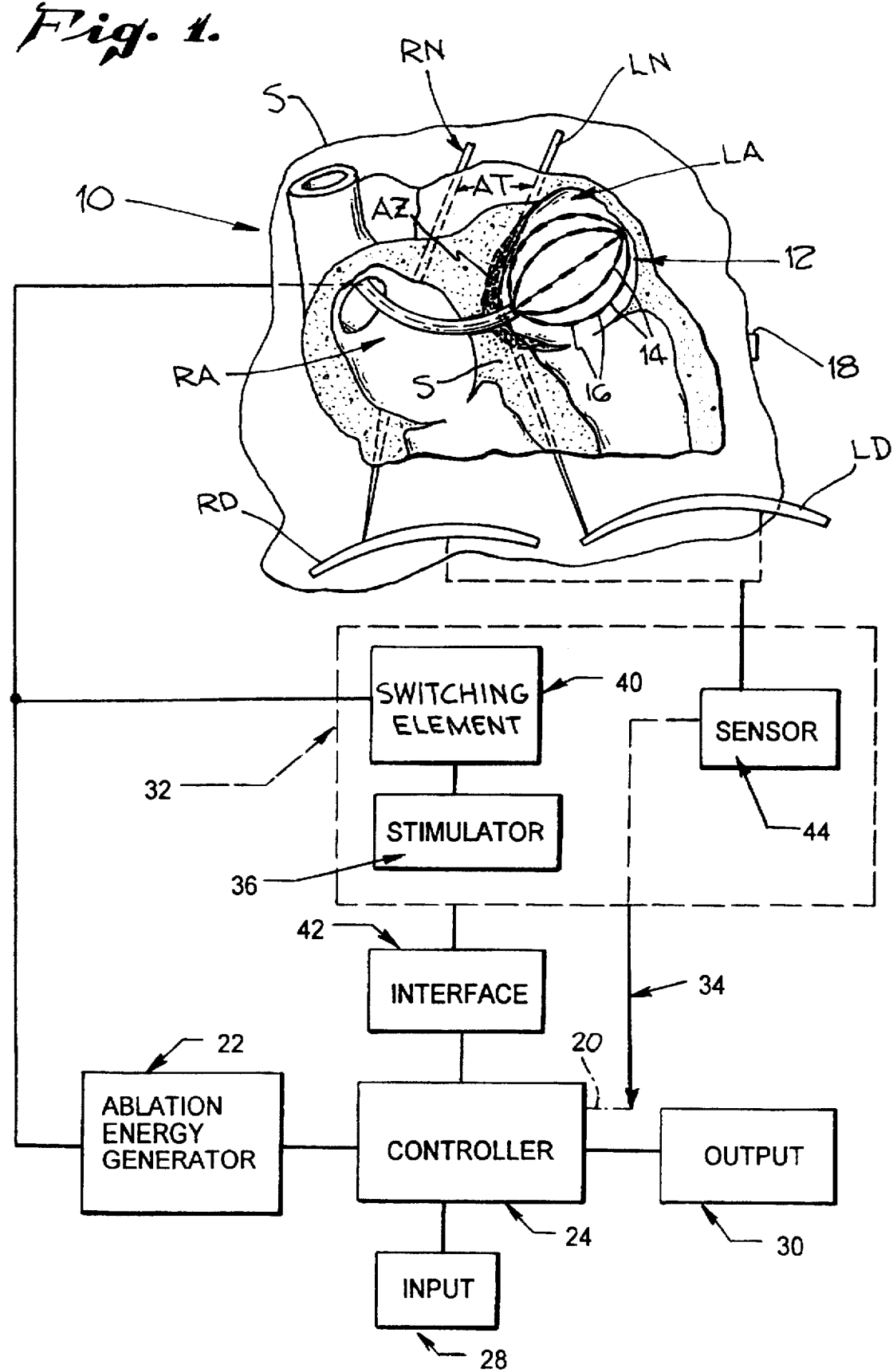

SYSTEM AND METHODS FOR DETECTING ANCILLARY TISSUE NEAR TISSUE TARGETED FOR ABLATION

FIELD OF THE INVENTION

In a general sense, the invention is directed to systems and methods for ablating interior regions of the human body. In a more particular sense, the invention is directed to systems and methods for ablating heart tissue for treating cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

For example, atrial geometry, atrial anisotropy, and histopathologic changes in the left or right atria can, alone or together, form anatomical obstacles. The obstacles can disrupt the normally uniform propagation of electrical impulses in the atria, resulting in abnormal, irregular heart rhythm, called atrial fibrillation. U.S. patent application Ser. No. 08/566,291, now U.S. Pat. No. 5,549,661 filed Dec. 1, 1995, and entitled "Systems and Methods for Creating Complex Lesion Patterns in Body Tissue" discloses catheter-based systems and methods that create complex long lesion patterns in myocardial tissue for the purpose of restoring uniform propagation of electrical impulses in the atria. In purpose and effect, the systems and methods emulate the open heart maze procedure, but do not require costly and expensive open heart surgery. These systems and methods can be used to perform other curative procedures in the heart as well.

As technology enabling the formation of larger or more complex lesion patterns in tissue continues to progress, it becomes increasingly important to detect, within a given tissue region targeted for ablation, the presence of ancillary tissue or anatomic structures that are not targeted for ablation.

SUMMARY OF THE INVENTION

The invention provides improved systems and methods for determining whether tissue or anatomic structures that are not targeted for ablation are present within a tissue region that is targeted for ablation.

In one embodiment, the systems and methods provide an operative element capable of supplying ablation energy to a region of tissue targeted for ablation. The systems and methods also provide a stimulator capable of applying within the region stimulant energy to affect a response from ancillary tissue not targeted for ablation. The systems and methods monitor the targeted tissue region where stimulant energy is applied and provide an output when ancillary tissue responds to the stimulant energy within the region.

In one embodiment, the operative element supplies energy to ablate a region of myocardial tissue. In this embodiment, the stimulator applies stimulant energy within the region to affect tissue that is not myocardial tissue. The systems and methods provide an output upon sensing that ancillary tissue is affected by the stimulant energy within the region.

In another embodiment, the systems and methods apply electrical energy pulses within the region targeted for ablation which are capable of stimulating response in phrenic nerve tissue. The systems and methods sense when diaphragm tissue served by the phrenic nerve tissue contracts in response to the applied electrical energy pulses. The systems and methods relocate the targeted ablation region so that diaphragm tissue no longer contracts in response to the applied electrical energy pulses. The systems and methods then apply ablation energy to the targeted region.

Other features and advantages of the inventions are set forth in the following Description and Drawings, as well as in the appended Claims.

BRIEF DESCRIPTION OF THE DRAWINGS

FIG. 1 shows a system for ablating heart tissue, which includes a module for determining whether tissue or anatomic structures that are not targeted for ablation are within a zone of tissue that is targeted for ablation.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows a system 10 for ablating an interior body region, e.g., the left atrium (LA). A transeptal deployment is shown, from the right atrium (RA) through the septum (S), into the left atrium (LA), where a multiple electrode ablation structure 12 is located for use. It should be noted that the heart shown in FIG. 1 is not intended to be anatomically accurate. FIG. 1 shows the heart in diagrammatic form to demonstrate the features of the invention.

It should also be appreciated that the invention is not limited in its application to cardiac ablation. The invention also has application in the diagnosis or treatment of intravascular ailments, in association, for example, with angioplasty or atherectomy techniques. The invention also has application for diagnosis or treatment of ailments in the gastrointestinal tract, the prostrate, brain, gall bladder, uterus, and other regions of the body. The invention can also be used in association with systems and methods that are not necessarily catheter-based.

The multiple electrode ablation structure 12 is shown in FIG. 1 because it is well suited for therapeutic use in the atrial regions of the heart. Longitudinal splines 14 on the structure carry an array of electrodes 16. The electrodes 16 serve as transmitters of radio frequency ablation energy, which is supplied by a generator 22. Of course, the ablation structure 12 can take other forms. For examples, the multiple ablation electrodes can be carried on the distal end of a catheter tube in the form of ring electrodes or wrapped wire coil electrodes. Alternatively, the ablation structure can comprise a single electrode carried at the distal end of a catheter tube. Of course, the single electrode embodiment leads to lesions having different characteristics than those formed by the multiple electrode array shown in FIG. 1.

The multiple electrodes 16 are preferably operated in a uni-polar mode, in which the radio frequency ablation energy transmitted by the electrodes 16 is returned through an indifferent patch electrode 18 externally attached to the skin (S) of the patient. Alternatively, the electrodes 16 can be operated in a bi-polar mode, in which ablation energy emitted by one or more electrodes 16 is returned an adjacent electrode 16 on the spline 14.

The ablation energy is characterized by its ability to ohmically heat myocardial tissue without electrically stimulating it. For example, high frequency radio frequency energy (500 kHz to 10 mHz) can be applied at current levels of from about 0.5 A to about 2.0 A to ohmically heat myocardial tissue without electrically stimulating it.

The size and spacing of the electrodes 16 shown in FIG. 1 are purposely set for creating continuous, long lesion patterns in tissue. Continuous, long lesion patterns are formed due to additive heating effects when RF ablation energy is applied in a uni-polar mode simultaneously to the adjacent electrodes 16, provided predetermined size and spacing requirements are observed. The additive heating effects cause the lesion pattern to span adjacent, spaced apart electrodes 16, creating the desired elongated geometry. The additive heating effects will also occur when the electrodes 16 are operated simultaneously in a bipolar mode between electrodes 16, again provided predetermined size and spacing requirements are observed. The predetermined size and spacing requirements generally require spacing between the electrodes 16 to be equal to or less than about 3 times the smallest of the diameters of the electrodes 16, or, alternatively, spacing between the electrodes 16 to be equal to or less than about 2 times the longest of the lengths of the electrodes 16.

Further details of the creation of complex long lesion patterns in the treatment of atrial fibrillation are found in copending U.S. application Ser. No. 08/566,291, filed Dec. 1, 1995, and entitled "Systems and Methods for Creating Complex Lesion Patterns in Body Tissue," which is incorporated herein by reference.

The system 10 includes a controller 24 coupled to the radio frequency generator 22. The controller 24 includes an interactive user interface, which includes an input device 28 (for example, a key board or mouse) and an output display device 30 (for example, a graphics display monitor or CRT). The controller 24 receives desired ablation control parameters from the user through the input device 28. The controller 24 conditions the generator to supply radio frequency energy to the electrodes 16 according to the desired control parameters. Preferably, the structure 12 carries temperature sensing elements (not shown), which provide tissue temperature feedback information to aid in the control of the ablation process.

The system 10 further includes a module 32 coupled to the controller 24. The module 32 determines whether ancillary tissue or anatomic structure (generally designated AT in FIG. 1), which is not targeted for ablation, nevertheless lies within the targeted zone where ablation energy is to be delivered by the electrodes 16. The delivery zone is generally designated AZ in FIG. 1.

The module 32 provides an output 34 indicative of the presence (or absence) of ancillary tissue or structures (AT) within the ablation energy delivery zone (AZ). The output 34 aids the physician in positioning the ablation structure 12 to best target the ablation energy to the desired region and away from ancillary tissue or structure (AT).

For purpose of illustrating operation of the module 34, FIG. 1 shows the ancillary tissue or structure (AT) to be the left phrenic nerve (designated LN in FIG. 1) and the right phrenic nerve (designated RN in FIG. 1). The left phrenic nerve (LN), which controls the response of the left diaphragm (designated LD in FIG. 1), is positioned over the left atrium (LA). The right phrenic nerve (RN), which controls the response of the right diaphragm (designated RD in FIG. 1), is positioned on the pericardium over the right atrium (RA). For purposes of illustration, FIG. 1 shows the left phrenic nerve (LN) lying within the ablation energy delivery zone (AZ) and the right phrenic nerve (RN) lying outside the deliver zone (AZ).

The module 34 includes an ancillary tissue stimulator 36. The purpose of the stimulator 36 is to apply stimulant energy, which is capable of invoking a physiological response from the ancillary tissue or structure (AT). The phrenic nerves (LN and RN) are capable of being stimulated by electrical pulses, which in turn leads to a contraction of the associated diaphragm (respectively LD and RD).

Stimulant energy for electrically stimulated tissue like skeletal or nerve tissue is characterized by its ability to electrically stimulate the tissue without ohmically heating it. Electrically stimulated tissue is very sensitive to low frequency electrical energy (less than about 10 kHz). Due to the sensitivity of the tissue, low frequency energy will electrically stimulate the tissue even at low current levels (e.g., from about 3 mA to about 20 mA), which do not cause an ohmic heating effect. The stimulant energy is preferably applied as square pulses having a pulse width of between about 0.1 msec to about 2 msec, with a repetition rate of about 1 to about 3 pulses per second. The magnitude of the applied stimulant energy represents less than one-millionth the magnitude of power applied to ablate tissue.

In the illustrated embodiment (where the ancillary tissue is electrically stimulated), the stimulator 36 comprises an electrical pulse generator. A switching element 40 distributes electrical pulses generated by the pulse generator 36 to one or more selected electrodes 16. The indifferent patch electrode 18 can serve as the return path for the electrical pulses (unipolar mode). Alternatively, an electrode 16 on the structure 12 adjacent to the pulse transmitting electrode 16 on the structure 12 can serve as the return path (bipolar mode).

The strength and sequence of electrical pulses are governed through an interface 42 by the controller 24. The electrical pulses must provide enough voltage or current to the selected electrode to locally stimulate the ancillary tissue (which, in the illustrated embodiment, is a phrenic nerve). In the illustrated embodiment, where the ablation-targeted tissue is also electrically stimulated tissue (myocardial tissue or skeletal muscle in general), the strength and cycle of electrical pulses usually will also stimulate the ablation-targeted tissue. If the ablation-targeted tissue is not electrically stimulated tissue, the electrical stimulant energy will not have a stimulant effect upon the ablation-targeted tissue.

In the context of the illustrated embodiment, where the ancillary tissue is phrenic nerve tissue, it is believed that the electrical pulses should comprise single, relatively wide pulses, in magnitude of about 3 mA to about 20 mA (3 to 20 Volts) with a pulse width from about 0.1 msec to about 2 msec, and with no grouping of multiple pulses. In the context of the illustrated embodiment, the electrical pulses are delivered at a rate faster than the normal breathing rate, so that a direct response to the stimulant energy can be discerned and distinguished over a normal coordinated response.

The module 34 includes a response sensor 44. The sensor 44 monitors physiologic activity and provides output indicative of a response (or lack of response) to the stimulant energy. In the context of the illustrated embodiment, the sensor 44 monitors the contraction of the left diaphragm (LD) and the right diaphragm (RD), while the stimulator 36 supplies the selected stimulant energy.

The sensor 44 can take various forms. In the illustrated embodiment, the sensor 44 comprises a fluoroscope. Alternatively, movement of the abdomen can be either visually observed or electrically monitored using an accelerometer or motion detector.

If the left phrenic nerve (LN) lies within the ablation energy delivery zone (AZ) of a given electrode 16, the stimulant energy supplied by the stimulator 36 and transmitted by that electrode 16 will cause the rate of contraction of the left diaphragm (LD) to increase. Likewise, if the right phrenic nerve (RN) lies within the ablation energy delivery zone (AZ) of a given electrode 16, stimulant energy supplied by the stimulator 36 and transmitted by that electrode 16 will cause the rate of contraction of the right diaphragm (RD) to increase. The application of stimulant energy of the character described above will evoke a sudden contraction of the diaphragm in the form of a strong twitch or "hiccup-like" response, unlike a coordinated normal breathing response.

If the particular phrenic nerve lies outside the ablation delivery zone, no increased rate of contraction for the diaphragm served by the phrenic nerve will be observed. Since the response of the ablation-targeted tissue can be easily distinguished from the expected response from stimulating the ancillary tissue, the stimulation of the ancillary tissue can be readily determined, even when superimposed on a response from the ablation-targeted tissue.

The sensor 44 monitors the rate of contraction of the left and right diaphragms (LD and RD) while the stimulator 36 sequentially supplies the stimulant energy to different electrodes 16. In this embodiment, the fluoroscopic image constitutes the output 34. The physician can observe the fluoroscopic output 34 and discern whether there is a response directly affected by the stimulant energy for each selected electrode 16 or selected group of electrodes 16. The presence of a response to the stimulant energy indicates that the structure 12 could be relocated to avoid unintended exposure of the responding phrenic nerve to ablation energy.

Alternatively, the sensor 44 can provide the output 34 in a processed digital or analog form for input directly to the controller 24, as phantom connection line 20 indicates. For example, the output 34 can comprise signals indicating a Proximity Alert Output—Left Phrenic Nerve and/or Proximity Alert Output—Right Phrenic Nerve, if increased contraction of, respectively, the left diaphragm (ID) or right diaphragm (RD) is sensed in response to the stimulant energy. Otherwise, the processed output 34 can provide a default signal indicative of No Proximity Output.

In this arrangement, the module 32 electronically feeds the processed proximity-indicative output 34 to the controller 24. The output display device 30 can communicate the proximity-indicative output 34 to the physician, either visually or by means of an audible alarm, or both. The physician can relocate the structure 12, until the output 34 indicates the absence of ancillary tissue or structures (AT) within the ablation energy delivery zone (AZ). In this way, the module 32 aids the physician to minimize the possibility of unintentionally ablating or damaging ancillary tissue or structure.

It has been discovered that, surprisingly, stimulators developed to stimulate myocardial tissue (by pacing) can also be effective at stimulating the phrenic nerve and causing the diaphragm to contract. This is surprising, because of (i) the differences between conventional stimulation of neural tissue and conventional stimulation of muscle tissue in general, and (ii) the specific differences in the observed response to stimulation by skeletal muscle tissue (like the diaphragm) and myocardial tissue.

Neural tissue responds quickly to high frequency stimulation and recovers quickly after stimulation is stopped. Conventional neural stimulators therefore apply short pulses, each having pulse widths typically less than 0.1 msec, which are grouped together in multiple pulse bursts.

Muscle tissue responds to stimulation in a way different than neural tissue. Muscle tissue does not respond as quickly to stimulation, nor does it recover as quickly, as neural tissue. Therefore, as a general proposition, pulses of higher voltage are required to directly stimulate muscle tissue, compared to neural tissue.

Furthermore, the specific response of skeletal muscle tissue to direct stimulation differs significantly from the specific response to myocardial muscle tissue to direct stimulation. When stimulated by multiple pulse bursts, skeletal tissue responds by contracting vigorously in a summation effect, which intensifies the contraction as the number of multiple pulse bursts increases. Myocardial tissue, on the other hand, does not exhibit the summation effect. Myocardial tissue responds to an initial stimulant pulse, and then becomes absolutely refractory for a period of time, during which time stimulant pulses have no effect. Thus, conventional heart pacing stimulators provide stimulant energy in single pulses having relatively wide pulse widths, typically greater than 0.1 msec and upward to 2 msec.

As above described, the system 10 applies stimulant energy to neural tissue in generally the same way as prior devices have applied pacing pulses to myocardial tissue. Conventional wisdom would lead one to conclude that cardiac-type pacing signals will not evoke a response in neural tissue. Convention wisdom would also say that higher frequency stimulation using pulse bursts of short pulse widths would be required. It is therefore surprising that cardiac-type stimulant energy, applied in the manner described above, possessing single, relatively wide pulses, and with no grouping of multiple pulses, affects any response in neural tissue of the phrenic nerve.

Conventional wisdom would also lead one to believe that cardiac-type pacing pulses will not evoke a noticeable response in skeletal tissue like the diaphragm. Conventional wisdom would say that stimulant energy in multiple pulse bursts is required to achieve a summation effect. It is therefore surprising that cardiac-type stimulant energy, applied in the manner described above, possessing single, relatively wide pulses, and with no grouping of multiple pulses, affects a readily discernable response in skeletal muscle like the diaphragm.

Various features of the invention are set forth in the following claims.

I claim:

1. A tissue ablation system for ablating tissue in a tissue region including ablation targeted tissue and ancillary tissue that is not myocardial tissue and is not targeted for ablation, the system comprising stimulator means for applying within the tissue region stimulant energy to affect ancillary tissue not targeted for ablation, and sensor means for providing a first output when the ancillary tissue is affected by the stimulant energy within the tissue region and a second output when the ancillary tissue is not affected by the stimulant energy, the second output being different than the first output.

2. A system according to claim 1, further comprising an ablation energy generator, and an operative element connected to the ablation energy generator, for supplying ablation energy to the tissue region.

3. A system according to claim 2
wherein the operative element includes at least one electrode.

4. A system according to claim 2
wherein the stimulator means is coupled to the operative element and the stimulant energy is applied through the operative element.

5. A system according to claim 1
wherein the stimulant energy comprises an electrical pulse.

6. A system according to claim 2
wherein the output indicates that the operative element should be relocated.

7. A tissue ablation system for ablating tissue in a tissue region including ablation targeted tissue and ancillary tissue that is not myocardial tissue and is not targeted for ablation, the system comprising
a source of radio frequency energy,
an operative element coupled to the source of radio frequency energy for transmitting the radio frequency energy to a region of tissue targeted for ablation,
a source of stimulant energy,
a stimulator coupled to the source of stimulant energy for applying the stimulant energy within the region to affect a response in ancillary tissue not targeted for ablation, and
a sensor for providing a first output when ancillary tissue responds to the stimulant energy within the region and a second output when the ancillary tissue is not is not affected by the stimulant energy, the second output being different than the first output.

8. A system according to claim 7
wherein the stimulant energy is not radio frequency energy.

9. A system according to claim 7
wherein the stimulator is coupled to the operative element to apply the stimulant energy through the operative element.

10. A system according to claim 7
wherein the operative element includes at least one electrode.

11. A system according to claim 7
wherein the stimulant energy comprises electrical energy.

12. A system according to claim 7
wherein the output indicates that the operative element should be relocated.

13. A system for ablating myocardial tissue in a myocardial tissue region including ablation targeted myocardial tissue and ancillary tissue that is not myocardial tissue, the system comprising
stimulator means for applying within the myocardial tissue region stimulant energy to affect the ancillary tissue that is not myocardial tissue, and
sensor means for providing a first output when the ancillary tissue is affected by the stimulant energy within the myocardial tissue region and a second output when the ancillary tissue is not affected by the stimulant energy, the second output being different than the first output.

14. A system according to claim 13, further comprising
an ablation energy generator, and
an operative element, connected to the ablation energy generator, for supplying ablation energy to the myocardial tissue region.

15. A system for ablating myocardial tissue in a myocardial tissue region including ablation targeted myocardial tissue and ancillary tissue that is not myocardial tissue, the system comprising
a source of radio frequency energy,
an operative element coupled to the source radio frequency energy for transmitting radio frequency energy to the region of myocardial tissue,
a source of stimulant energy,
a stimulator coupled to the source of stimulant energy for applying within the myocardial tissue region pulses of the stimulant energy to affect a response in ancillary tissue that is not myocardial tissue, and
a sensor for providing a first output when ancillary tissue responds to the stimulant energy within the myocardial tissue region and a second output when the ancillary tissue is not affected by the stimulant energy, the second output being different than the first output.

16. A system according to claim 14 or 15
wherein the operative element includes at least one electrode.

17. A system according to claim 14 or 15
wherein the operative element includes an array of electrodes.

18. A system according to claim 14 or 15
wherein the stimulator applies the stimulant energy through the operative element.

19. A system according to claim 14 or 15
wherein the output indicates that the operative element should be moved.

20. A method for detecting ancillary tissue that is not myocardial tissue and is not targeted for ablation within a tissue region including tissue targeted for ablation, the method comprising the steps of
locating the target tissue region,
applying stimulant energy within the target tissue region, the stimulant energy being such that tissue targeted for ablation will respond to the stimulant energy in a first predetermined manner and ancillary tissue not targeted for ablation will respond to the stimulant energy in a second predetermined manner, the second predetermined manner being different than the first predetermined manner, and
sensing whether ancillary tissue not targeted for ablation is affected by the stimulant energy within the target tissue region by determining whether tissue in the region responds in the second predetermined manner.

21. A method according to claim 20, further comprising the step of
relocating the target tissue region, in response to a determination that tissue in the region has responded in the second predetermined manner, until ancillary tissue ceases to be affected by stimulant energy applied within the target tissue region.

22. A method for detecting ancillary tissue within a myocardial tissue region targeted for ablation comprising the steps of
locating a target tissue region for ablation,
applying stimulant energy within the target tissue region to affect a response in ancillary tissue that is not myocardial tissue, and
sensing when the ancillary tissue responds to the stimulant energy within the target tissue region.

23. A method for ablating tissue within a zone targeted for ablation without ablating ancillary tissue that is not myocardial tissue and is not targeted for ablation comprising the steps of locating a region to apply ablation energy to tissue, applying stimulant energy within the region to affect ancillary tissue not targeted for ablation, sensing when the ancillary tissue is affected by the stimulant energy within the region, and relocating the region, in response to the sensing of ancillary tissue not targeted for ablation, until the ancillary tissue is not affected by the stimulant energy.

24. A method according to claim 23, further comprising the step of applying ablation energy in the target tissue region in response to a determination that ancillary tissue is not affected by the stimulant energy.

25. A method for ablating myocardial tissue targeted for ablation within a heart without ablating ancillary tissue that is not myocardial tissue comprising the steps of locating a region to apply ablation energy to myocardial tissue targeted for ablation, applying stimulant energy within the region to affect ancillary tissue that is not myocardial tissue, sensing when the ancillary tissue is affected by the stimulant energy within the region, and relocating the region, in response to the sensing of ancillary tissue not targeted for ablation, until the ancillary tissue is not affected by the stimulant energy.

26. A method according to claim 25, further comprising the step of applying ablation energy in the region in response to a determination that ancillary tissue is not affected by the stimulant energy.

27. A method for ablating myocardial tissue within a heart without ablating phrenic nerve tissue comprising the steps of locating a region to apply ablation energy to myocardial tissue, applying electrical energy pulses within the region to stimulate a response in phrenic nerve tissue, sensing when diaphragm tissue served by the phrenic nerve tissue contracts in response to the applied electrical energy pulses, and relocating the region until the diaphragm tissue does not contract in response to the applied electrical energy pulses, and applying ablation energy in the region.

28. A method according to claim 27 wherein the step of applying electrical energy pulses includes applying pulses of energy with a frequency of less than about 10 kHz.

29. A method according to claim 27 wherein the step of applying electrical energy pulses includes applying pulses of energy having a magnitude of between about 3 mA and about 20 mA and having a pulse width greater than about 0.1 msec.

* * * * *